US008900864B2

(12) United States Patent
Prante et al.

(10) Patent No.: US 8,900,864 B2
(45) Date of Patent: Dec. 2, 2014

(54) STABILIZED LEUKOCYTES AND THEIR USE

(75) Inventors: Christian Prante, Bielefeld (DE); Knut Kleesiek, Oeynhausen (DE); Wolfgang Prohaska, Oeynhausen (DE)

(73) Assignee: Nordrhein-Wesfalen Krankenhausbetriebsgesellschaft Bad Oeynhausen mbH, Bad Oeynhausen (DE)

( * ) Notice: Subject to any disclaimer, the term of this patent is extended or adjusted under 35 U.S.C. 154(b) by 20 days.

(21) Appl. No.: 13/825,227

(22) PCT Filed: Sep. 13, 2011

(86) PCT No.: PCT/EP2011/004599
§ 371 (c)(1),
(2), (4) Date: Mar. 20, 2013

(87) PCT Pub. No.: WO2012/038041
PCT Pub. Date: Mar. 29, 2012

(65) Prior Publication Data
US 2013/0183661 A1 Jul. 18, 2013

(30) Foreign Application Priority Data
Sep. 21, 2010 (EP) ..................... 10010012

(51) Int. Cl.
C12N 5/078 (2010.01)
A01N 1/02 (2006.01)
G01N 33/50 (2006.01)
G01N 33/569 (2006.01)

(52) U.S. Cl.
CPC ............ *C12N 5/0634* (2013.01); *A01N 1/0231* (2013.01); *G01N 33/505* (2013.01); *G01N 33/56988* (2013.01)
USPC .................. 435/374; 435/5; 435/29

(58) Field of Classification Search
CPC . A01N 1/0231; C12N 5/0634; G01N 33/505; G01N 33/56988
See application file for complete search history.

(56) References Cited

U.S. PATENT DOCUMENTS 5,478,722 A 12/1995 Caldwell

FOREIGN PATENT DOCUMENTS

| CN | 101 363 846 A | 2/2009 |
| EP | 1 217 372 A1 | 6/2002 |
| WO | 2010/078194 A1 | 7/2010 |

OTHER PUBLICATIONS

Svendentsov et al. Leukocyte Preservation at Near-Zero Temperatures. Human Physiology 2010, vol. 36, No. 3, pp. 360-363.*
Phillips et al. 2008, Lancet 317:1443 See Spec., p. 1 Outcomes from monitoring of patients on antiretroviral therapy in resource-limited settings with viral load, CD4 cell count, or clinical observation alone: a computer simulation model.
Paintsil et al. 2008, Pdiatr. Infec Dis J; 27(7):629 See Spec., p. 1 Absolute CD4+ T-Lymphocyte Count as a Surrogate Marker of Pediatric HIV Disease Progression.
Ledergerber et al. 2004, Lancet: 364:51 See Spec., p. 1 Predictors of trend in CD4-positive T-cell count and mortality among HIV-1-infected individuals with virological failure to all three antiretroviral-drug classes.
Plate et al. 2009, Viral Immunol. 22(5):329 See Spec., p. 2 Evaluation of the Blood Stabilizers TransFix and Cyto-Chex BCT for Low-Cost CD4 T-Cell Methodologies.
Truett et al. 2006, Jacquir Immune Defec Syndr, 41(2):168 See Spec., p. 2 Efficacy of Cyto-Chex Blood Preservative for Delayed Manual CD4 Testing Using Dynal T4 Quant CD4 Test Among HIV-Infected Persons in Zambia.
O'Gorman et al. 2008 Cytometry B Clin Cytom 74 Suppl 1:19 See Spec., p. 2 CD4 T Cell Measurements in the Management of Antiretroviral Therapy—A Review with an Emphasis on Pediatric HIV-Infected Patients.
Bergeron et al. 2009, Cytometry B Clin Cytom See Spec., p. 2 Evaluation of a Dry Format Reagent Alternative for CD4 T-Cell Enumeration for the FACSCount System: A Report on a Moroccan-Canadian Study.
Pattanapanyasat et al. 2005, J Med Res; 121(4):539 See Spec., p. 2 CD4+ T cell count as a tool to monitor HIV progression & antiretroviral therapy.
D. E. Campbell et al.: "Analytical and Biological Considerations in the Measurement of Cell-Associated CCR5 and CXCR4 mRNA and Protein", Clinical and Vaccione Immunology, Vo. 17, No. 7, May 12, 2010, pp. 1148-1154 See International Search.

* cited by examiner

*Primary Examiner* — Louise Humphrey
(74) *Attorney, Agent, or Firm* — Davis & Bujold, PLLC; Michael J. Bujold

(57) ABSTRACT

A method of producing extremely stable leukocytes from human blood samples which are stable for long period of time under extraordinary temperature conditions. The method also relates to producing and stabilizing the leukocytes with formaldehyde release agents. The method is directed at the use of the stabilized leukocytes as a control in assays for determining CD4+ and HIV diagnosis and therapy.

20 Claims, 8 Drawing Sheets

STABILIZED LEUKOCYTES AND THEIR USE

Figure 1:
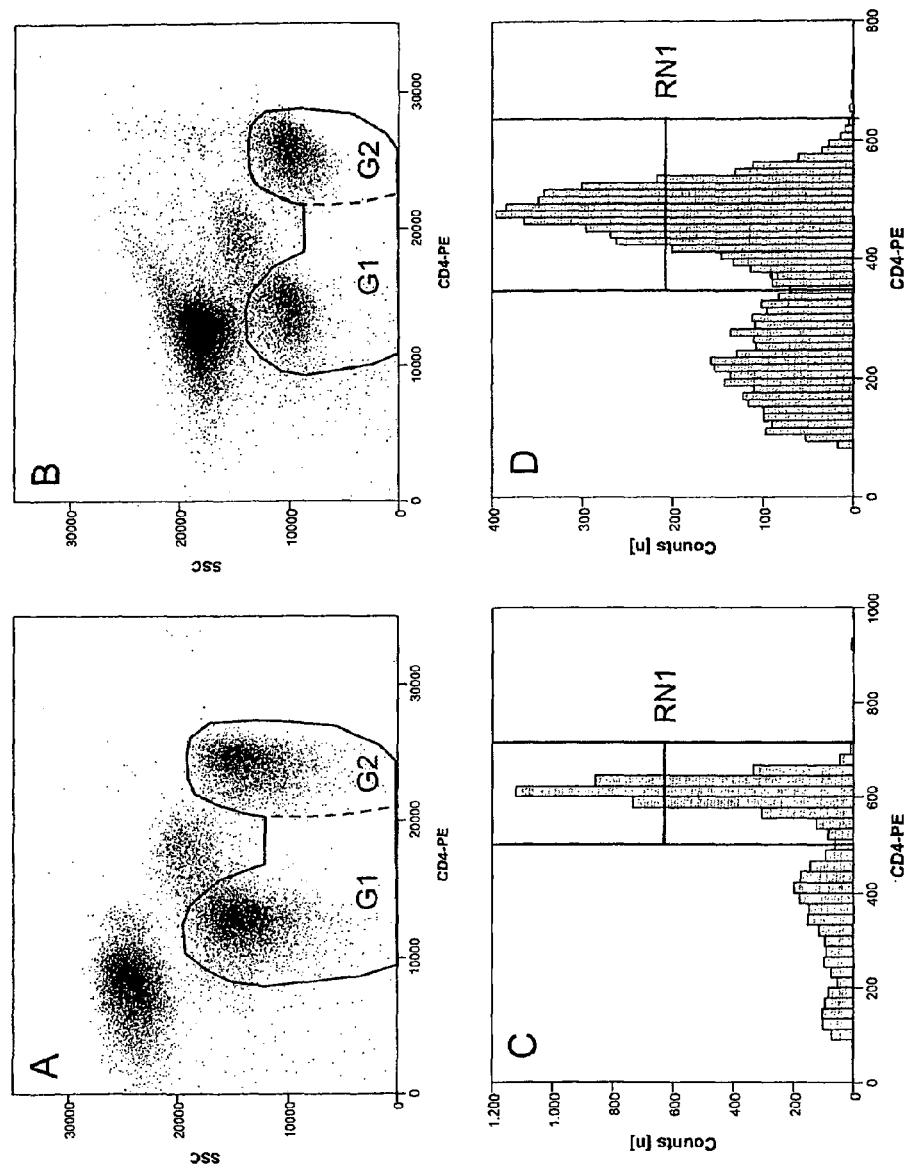

This application is a National Stage completion of PCT/EP2011/004599 filed Sep. 13, 2011, which claims priority from European patent application serial no. 10 010 012.2 filed Sep. 21, 2010.

FIELD OF THE INVENTION

This invention relates to a method of producing extremely stable leukocytes from human blood samples which are stable for a long period under extraordinary temperature conditions. In particular, the invention relates to a method of stabilizing and producing said leukocytes by means of formaldehyde releasing agents. The invention is finally directed to the use of said stabilized leukocytes as control in assays for determining CD4+ cells in HIV diagnosis and therapy.

BACKGROUND OF THE INVENTION

The diagnosis and antiviral therapy of HIV/AIDS is a major challenge in developing countries. Thus, the accurate determination of CD4+ T-cells is of major importance. Different trials have been started to develop an international external quality control for this immunological measurement. The main problem with implementing inter-laboratory tests in countries with resource-limited settings is the insufficient stability of fresh blood samples. For an international distribution, stabilized blood samples are required which can withstand shipment throughout the global, mainly tropical hemisphere. In order to solve this problem we have developed a new method of generating freeze-dried leukocytes which are suitable for long-term storage at elevated temperatures CD4+ T-cells are also known as helper T-cells and act as an co-ordinator of the immune response, unfortunately, CD4+ T-cells are also the main targets of HIV. HIV destroys infected CD4+ T-cells and leading to an overall weakening of the immune system.

The monitoring of CD4 T-cell counts has been well established as a surrogate marker for the therapy of HIV/AIDS (Phillips et al. 2008, Lancet 317:1443; Paintsil et al. 2008, Pdiatr. Infect Dis J; 27(7):629). The decision of when to switch the therapeutic regime from first to second line depends on the concentration of CD4+ T-cells (Ledergerber et al. 2004, Lancet: 364:51).

Lower numbers of circulating CD4+ T-cells indicates a weakening of the immune system and advancement in the progression of HIV disease. The CD4+ T-cell count can also be indicative of the success or failure of anti-retroviral therapy (ARV).

In countries with a high prevalence of HIV/AIDS and resource-limited settings, different affordable devices based on flow cytometry are available to determine the CD4+ count and CD4+ percentage of lymphocytes. Thus, the accuracy of measurements in regional testing facilities is a critical point involving several problems. To date, no international external quality assurance/quality control (QA/QC) programs for CD4 count and CD4 percentage in resource-limited settings exist. This is mainly due to the fact that cold chains or refrigeration during transportation and storage of control materials cannot be realized in many countries within the southern hemisphere.

Cytometric monitoring is being used for most of the 2 million patients currently receiving antiretroviral therapy in these countries. Commercially available fluid control materials like Cyto-Chex (Streck, USA) or Transfix (Cytomark, UK), based on stabilized blood cells, have a limited shelf life and are not stable enough for long transportation routes at elevated temperatures (Plate et al. 2009, Viral Immunol. 22(5):329; Truett et al. 2006, J Acquir Immune Defec Syndr, 41(2): 168). The effect of storage temperature has been investigated in several publications using different approaches to achieve blood preservation.

The correct determination of the CD4+ count and CD4+ percentage has significant implications for effective management of the individual antiretroviral HIV therapy (O'Gorman et al. 2008, Cytometry B Clin Cytom 74 Suppl 1:19). Therefore, it is essential that external QA/QC programs are implemented in countries with a high prevalence of HIV/AIDS. Several attempts have already been made to generate suitable control materials for flow cytometric CD4 analysis in regional facilities (Bergeron et al. 2009, Cytometry B Clin Cytom). Without a proper cooling chain, no durable cellular control material that contains leukocytes for flow cytometric CD4 monitoring is available to date. Commonly used preparations consist of chemically stabilized suspensions of whole blood with a maximum shelf life at ambient temperature (25-37° C.) of 2 weeks (Pattanapanyasat et al. 2005, J Med Res; 121(4):539). In practice, this time frame is often not sufficient for reliable usage in QA/QC programs. Currently used stable materials for internal or external quality controls are based on polystyrene or latex beads. Control beads and native blood samples are generally processed with different instrument settings. Concerning this matter, the usage of preserved human leukocytes for flow cytometric QC/QA has the advantage of being a full process control.

Until now, no adequate method has been found to preserve leukocytes with a durability of more than 2 weeks at 37° C. (Plate et al. 2009, Viral Immunol. 22(5):329), let alone for the conditions regarding transport times and ambient temperature prevailing in many countries within the southern hemisphere. Commercially available lyophilized lymphocytes or polystyrene and latex beads have the disadvantage of being almost artificial because they do not exhibit the same flow cytometric appearance as native blood, which is an important requirement for QA/QC programs.

Therefore, the problem of the invention to be solved was to provide a method of stabilizing leukocytes from human blood samples, wherein the stabilized leukocytes are comparable in function and activity with leukocytes freshly isolated from blood.

SUMMARY OF THE INVENTION

The invention discloses in general a new method of producing stable lyophilized leukocytes, wherein said leukocytes are isolated from blood. In more detail the invention is related to the production of long-term durable leukocytes prepared from human blood as a quality control material for flow cytometric analysis or other suitable analytic methods that can withstand transport and storage at elevated temperatures, which are common for many African and South Asian countries. After re-suspension after four and more weeks these stabilized cells are suitable for common flow cytometric gating strategies. The method according to the invention includes stabilization of preferably human leukocytes preferably from blood samples by means of formaldehyde releasing agents, and is applicable to leukocytes from healthy humans as control material as well as from patients suffering from a disease which is related to modulated CD4+ T cell expression, such as HIV/AIDS.

Thus, it is an object according to this invention, to provide an in-vitro method for stabilizing leukocytes comprising incubating leukocytes isolated from a blood sample for at least 12 hours, such as between 12 and 48 h, preferably at least 24 h, and most preferably 24 to 28 h, in a solution comprising a formaldehyde releasing agent, preferably IU, followed by lyophilization of the incubation solution resulting in a long-term stable lyophilized preparation.

It is a further object of the invention to provide an in-vitro method of determining and/or monitoring the count and/or percentage of CD4+ T cells in a sample, the method comprising using a long-term durable leukocyte preparation comprising leukocytes isolated from a blood sample that were stabilized prior to lyophilization by means of a formaldehyde releasing compound.

It has been found that leukocytes isolated from human blood followed by direct lyophilization are not stable enough for a longer time even under moderate conditions. However, if these leukocytes are stabilized prior to lyophilization with a formaldehyde releasing agent, preferably imidazolidinyl urea (IU), the resulting lyophilized leukocyte preparation is extremely stable even at temperatures up to 40° C. and higher and after storage at high temperatures for more than one month.

The resuspended lyophilized preparation does not lose its activity regarding the counts/percentage of functionally active CD4+ T cells. Above all, these stable leukocytes if re-suspended, exhibit the same flow cytometric appearance and properties as compared with leukocytes isolated from native fresh blood. This is an important requirement for standardized quality analysis (QA) and quality control (QC) programs. Moreover, the leukocyte preparation obtained by the method according to the invention is further characterized by the fact that the lyophilized leukocytes can be re-suspended by at least 95%, preferably by 99-100%, in an aqueous solution after a long-term storage of at least four weeks.

In summary the invention is directed to the following subject-matters:

An in-vitro method for stabilizing leukocytes, preferably isolated from (human) blood samples, comprising incubating leukocytes for at least 12 hours, preferably 24-28 hours, in a solution comprising a formaldehyde releasing agent, followed by lyophilization of the incubation solution resulting in a long-term stable lyophilized preparation.

A respective method, wherein the formaldehyde releasing agent is preferably dissolved or suspended in an aqueous buffered solution, preferably comprising polyethylene glycol (PEG) in a concentration of 0.5-15% by weight of the overall composition, preferably 1-15%, more preferably 4-7%, more preferably 3-6%, and more preferably 3-4%.

A respective method, wherein the formaldehyde releasing agent is imidazolidinyl urea (IU) or diazolidinyl urea (DU), preferably IU.

A respective method, wherein leukocytes comprise CD4+ receptor bearing cells, such as lymphocytes or monocytes, are isolated from other blood components of the blood sample by density gradient centrifugation, preferably carried out at 700-1000 g, preferably 800-1000 g, more preferably at or around 800 g for at least 20 minutes, preferably in a separation medium having a density of δ=1.080 until 1.100, preferably 1,090 until 1.095.

A respective method, wherein the leukocyte preparation comprises granulocytes, thus simulating a blood-similar testing assay.

A respective in-vitro method of determining and/or monitoring the count and/or percentage of CD4+ T cells in a sample, the method comprising using a long-term durable leukocyte preparation comprising leukocytes isolated from a blood sample, preferably a human blood sample, that were stabilized prior to lyophilization by means of a formaldehyde releasing compound, preferably IU.

A respective method, wherein the determination of the CD4+ T cells is carried out by means of flow cytometry.

A long-term stable preparation of lyophilized leukocyte preparation obtained by a method described above and below, wherein the lyophilized product has 0-3%, preferably 1-2% (w/w), moisture content.

A corresponding stabilized preparation, wherein said stabilized lyophilized leukocytes are resuspendable in an aqueous solution by at least 95%, preferably 99-100% after at least 4 weeks storage, thereby showing full CD4+ T cell activity.

A respective preparation for use for the diagnosis and treatment of a disease, preferably HIV/AIDS, accompanied by a decrease or increase of CD4+ T cells in the blood; or the use of said respective preparation for the in-vitro diagnosis of a disease, preferably HIV/AIDS, accompanied by a decrease or increase of CD4+ T cells in the blood.

The use of the long-term durable leukocyte preparation as specified in an in vitro assay for determining CD4+ T cells.

A respective use as control and/or calibration material in an in-vitro assay for determining CD4+ T cells from fresh blood samples.

A respective use in an in-vitro assay for diagnosing HIV/AIDS.

DETAILS OF THE INVENTION

Formaldehyde releasing agents are known in the art. The use of formaldehyde releasing agents for fixation and storage of tissues, cells and cell components in connection with (immuno-)histological investigations is also well known. Thus, WO 1994/07532 describes a fixative solution for tissues and cells comprising histological fixing amounts of an antigenic preserving formaldehyde donor in a polar solvent. The patent application discloses several suitable agents such as diazolidinyl urea (DU) and imidazolidinyl urea (IU). The agents are used in solution to preserve a cell suspension while measuring cells by flow cytometry in a flow chamber. US 2002/0119503 describes a reagent composition for preparing leukocytes from human blood for analysis by flow cytometry comprising a lipoprotein such as cholesterol, an agent for lysing erythrocytes such as saponin, and optionally a preservative, such as DU or IU, for protecting the cell suspension during measurement with a cytometer. WO2010/078194 teaches a method for screening a blood product for transfusion purposes comprising contacting a leukocyte-reduced blood sample with a screening preservative composition, e.g. containing IU or DU, in a substantially solid state form and screening any residual leukocytes prior to blood transfusion. Other patents e.g. U.S. Pat. No. 5,858,699; U.S. Pat. No. &,579,672) are directed to the treatment of leukocytes with transition metal solutions in order to stabilize leukocyte preparations for a diversity of applications. This approach is marketed under the trade name TRANSFIX.

The formaldehyde releasing agent according to the invention comprise imidazolidinyl urea (IU) or diazolidinyl urea (DU) and mixtures thereof.

Recently IUPAC corrected the old erroneous old structure of IU, which is 1,1'-methylene-bis{3-[1-(hydroxymethyl)-2,5-dioxoimidazolidin-4-yl]urea} to the new correct structure: 1,1'-methylene-bis{3-[3-(hydroxymethyl)-2,5-dioxoimidazolidin-4-yl]urea}

IU is a condensation product of allantoin and formaldehyde with the trade name Germall 115™ and is commonly used as an antimicrobial preservative in cosmetics. In aqueous solution it dissociates into several compounds: (4-hydroxymethyl-2,5-dioxo-imidazolidin-4-yl)-urea, allantoin and unidentified minor presumably formaldehyde-releasing compounds. Until now, the stabilizing mechanism of IU on cells is not clearly known (Lehmann et al. 2006, Contact Dermatitis 54(1):50). IU may exhibit its preservative properties by releasing formaldehyde or by action of the parent chemical structure of the compound. The usage of IU for preservation of blood samples has the additional benefit of being antibacterial as well as antimycotic (Berke et al. 1970, Am Perfum Cosmet 85:55).

However, although IU is a preferred formaldehyde releasing agent according to this invention, other commonly used formaldehyde releasing agent are also applicable. IU is however preferred, because the inventors found that this compound provides the most stable leukocyte preparations according to the invention as compared with other formaldehyde releasing agents, including formaldehyde as such.

Suitable formaldehyde agents according to the invention are, without limiting the scope of the invention:

Imidazolidinyl Urea (CAS RN: 39236-46-9) (IU)
Diazolidinyl Urea (CAS RN: 78491-02-8) (DU)
1,3-Dimethylol-5,5-dimethylhydantoin (CAS RN: 6440-58-0)
Bronopol (CAS RN: 52-51-7)
Tris(hydroxymethyl)nitromethane (CAS RN: 126-11-4)
Polyethylene glycol sorbitan monolaurate (CAS RN: 9005-64-5)
Poly(acrylamide, trimethylaminoethyl methacrylate chloride) (CAS RN: 35429-19-7)

In principal, those formaldehyde releasing agents are preferred according to the invention that generate stabilized lyophilized leukocytes, which can be easily resuspended in an aqueous solution having full CD4+ T cell activity by a percentage of at least 95%, at least 96%, at least 97%, at least 98%, at least 99%, or 100% after at least 4, 5, 6, 7 or 8 weeks. With IU and DU lyophilized leukocytes can be obtained which are by at least 99% re-suspendable after at least 4 weeks, preferably at least 6 weeks.

To fulfill the difficult requirements for international distribution to developing countries within the southern hemisphere this invention describes a new method of preparing stabilized leukocytes which can withstand long transportation routes at high temperatures. The combination of chemical fixation with a formaldehyde releasing agent, preferably IU, and subsequent freeze-drying provides an opportunity to extend shelf life at elevated temperatures significantly.

These studies show that the leukocyte samples prepared by the method of the invention exhibit an almost native flow cytometric scatter (FIG. 1) and can withstand a storage temperature of about 40° C. for more than 4 weeks, preferably between 4-8 weeks, without any signs of degradation (FIGS. 2, 3). With regard to an international pilot survey, the inventors received no reports of problems with the preserved test samples when applying commonly used gating strategies. Data sheets from several participants showed that samples sustained their morphological and immunological phenotype after transport to Africa and Asia. The two different methods used by participants for the determination of CD4+ T-cells (CD4 absolute and CD4 percentage, see methods/flow cytometry) revealed the same target values without significant variations. No significant correlation between the age of the samples and variations from the target value was observed. The mean time of transport for test samples was 9.2 days (±6.2 d), with a maximum delivery time of 29 days.

It should be mentioned that human blood essentially consists of erythrocytes and leukocytes. The blood leukocytes comprise different cells such as granulocytes, lymphocytes, monocytes. Lymphocytes and monocytes have CD4+ receptors on their surface and, thus, are the sub-cell population of said leukocytes which is preferred according to the invention. The different cells are of different size and can be separated by density gradient centrifugation according to well-known standard methods. The preferred values of density gradient centrifugation for separating leukocytes according to the invention comprising all sub populations including granulocytes, are 700-1000 g, preferably 800 g (±10%) at a density of 1.090 to 1.100, thus this fraction contains essentially all leukocyte subpopulations, including granulocytes. However, according to the invention, it is also possible to separate granulocytes, and to use a granulocyte-free fraction of leukocytes for stabilization. Granulocytes are known not to be very stable in-vitro. For that reason, it is more advantageous to separate them from blood before testing blood samples. Surprisingly, according to the invention a leukocyte fraction from blood which still contains granulocytes is after treatment with the formaldehyde releasing agent according to the invention as stable as a leukocyte fraction from which the granulocytes were separated prior to said treatment. Thus, by the method according to the invention, also granulocytes can be stabilized, and it is not necessary to separate them by an addition separation step from the other leukocytes.

Data from the pilot survey approved that lyophilized cells exhibit a significantly longer shelf life than fluid preparations. Using preserved biological probes for flow cytometric quality control has the advantage of being a full process control with a normal scatter diagram. The inventors could demonstrate that an international distribution of lyophilized leukocytes for the flow cytometric quality control is feasible. There is an urgent need for stable control material for flow cytometric analysis in order to guarantee accurate, standardized antiretroviral therapy in developing countries with a high prevalence of HIV/AIDS. In cooperation with the Reference Institute for Bionalytics (RfB, Germany) from the German Society for Clinical Chemistry and Laboratory Medicine (DGKL), these lyophilized samples have been shipped to 98 participants from 21 countries within the African and Asian continents and successfully used as external quality control material for CD4+ T-cell counting (Table 1).

Figure 2A:
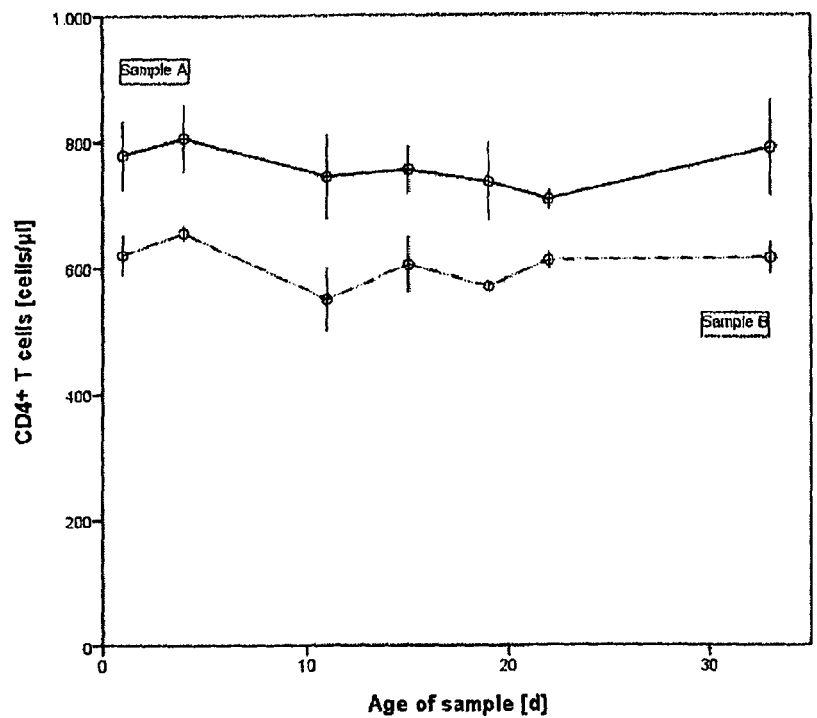
Figure 2B:
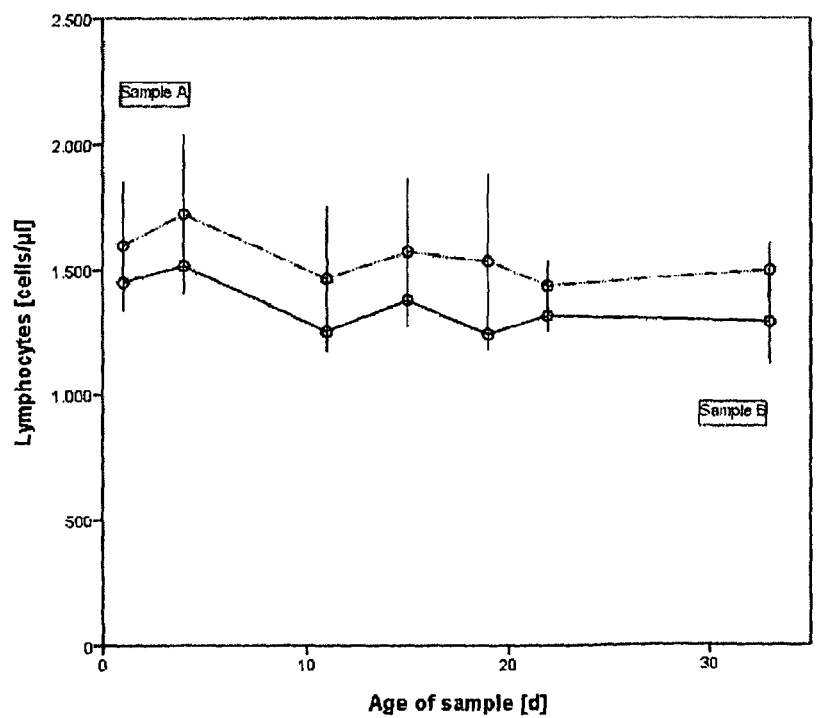
Figure 3A:
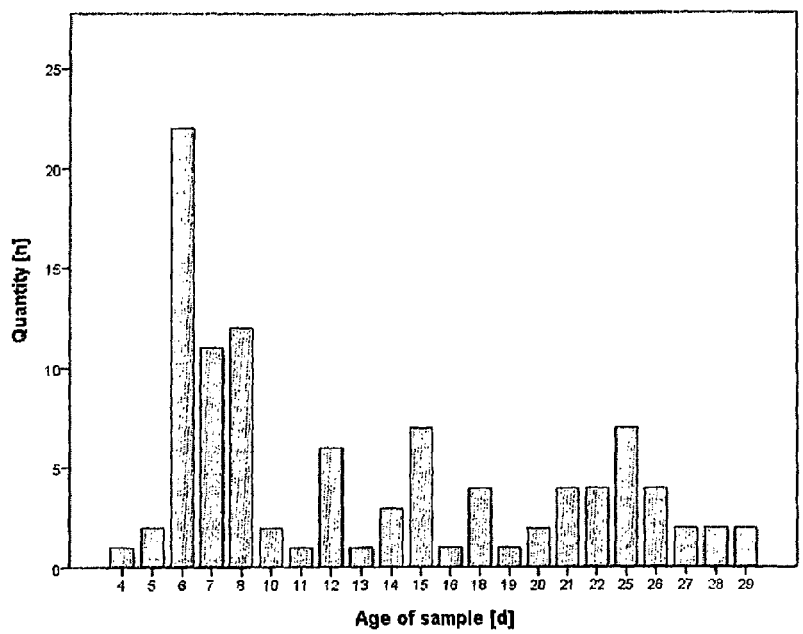

In order to test the long-term stability of the preserved leukocytes, freeze-dried aliquots were stored at 40° C. for up to 33 days. The flow cytometric analysis of rehydrated probes was performed at 3-day intervals. Lyophilized leukocytes showed no significant alteration regarding their morphological phenotype, the absolute CD4 count and lymphocyte count during 33 days of storage (FIGS. 2A, 2B). In parallel, the concentration of resuspended leukocytes determined by an impedance hematology analyzer (Sysmex K1000) showed no significant variance. The flow cytometric analysis revealed an intraday coefficient of variation for absolute CD4 T-cell count of 4.8% and 6.1% for CD4% of lymphocytes (n=10). These results correlate with data received from fresh blood preparations (Cassens et al. 2004, Antivir Ther 9(3):395). The interday coefficient of variation for CD4+ T-cells during time of storage (d=33) was 5.4%. For CD4% of lymphocytes we obtained an interday coefficient of variation of 7.6%.

Figure 3B:
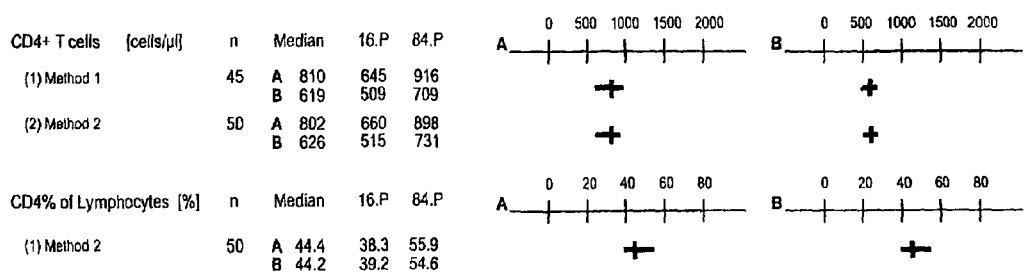
Figure 4A:
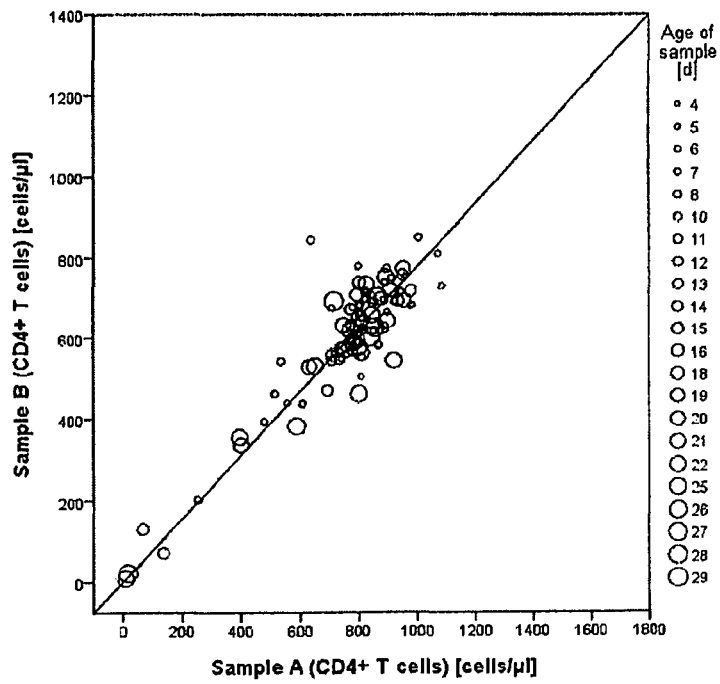
Figure 4B:
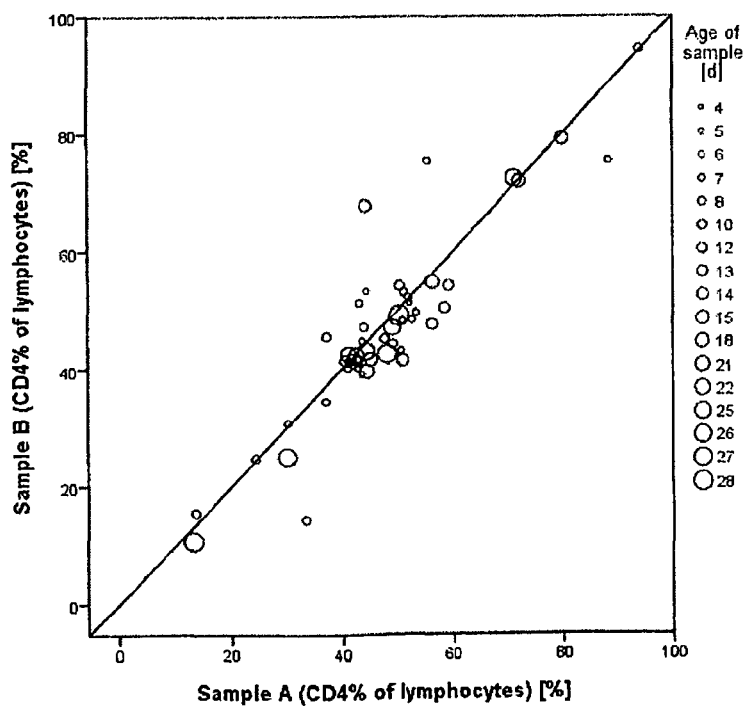

Samples of stabilized leukocytes were sent to 21 different countries within the African and Asian continents (Table 1) at ambient temperature without any cooling devices. The transportation time to the recipients varied from 1 week up to 4 weeks (FIG. 3A), with a mean shipping time of 14 days. Most of the participants were able to analyze the control samples. 88 out of 95 participants (92.6%) obtained good results for absolute CD4 count defined as SEM (standard error of mean) <26% independently of the used flow cytometric method (CD4 absolute or CD4%, see methods/flow cytometry) (FIG. 3B). There was no significant correlation between the age of the samples (transportation time) and the accuracy of values for the CD4 count and CD4 percentage of lymphocytes (FIG. 4).

Figure 5A:
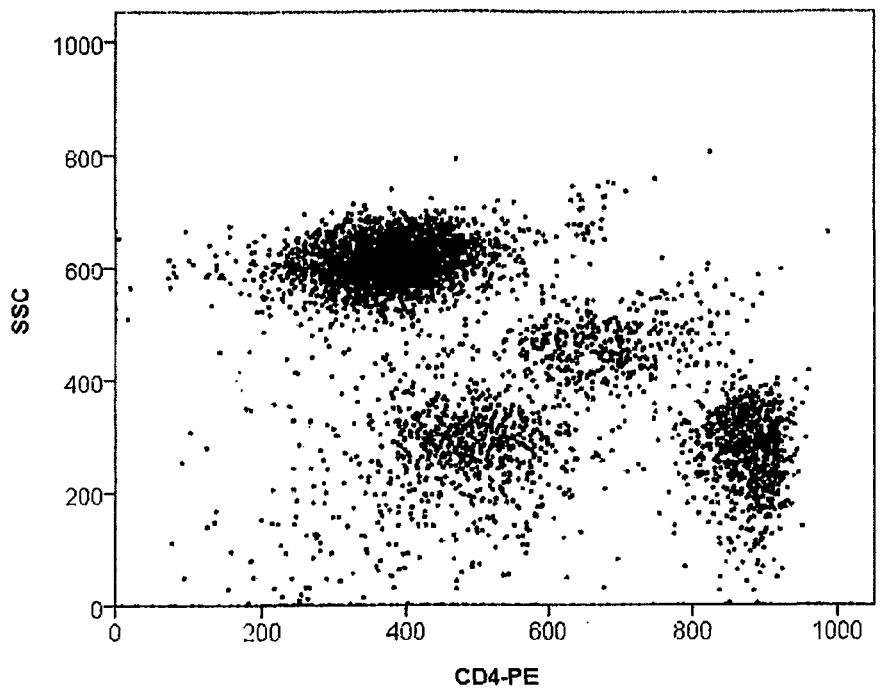
Figure 5B:
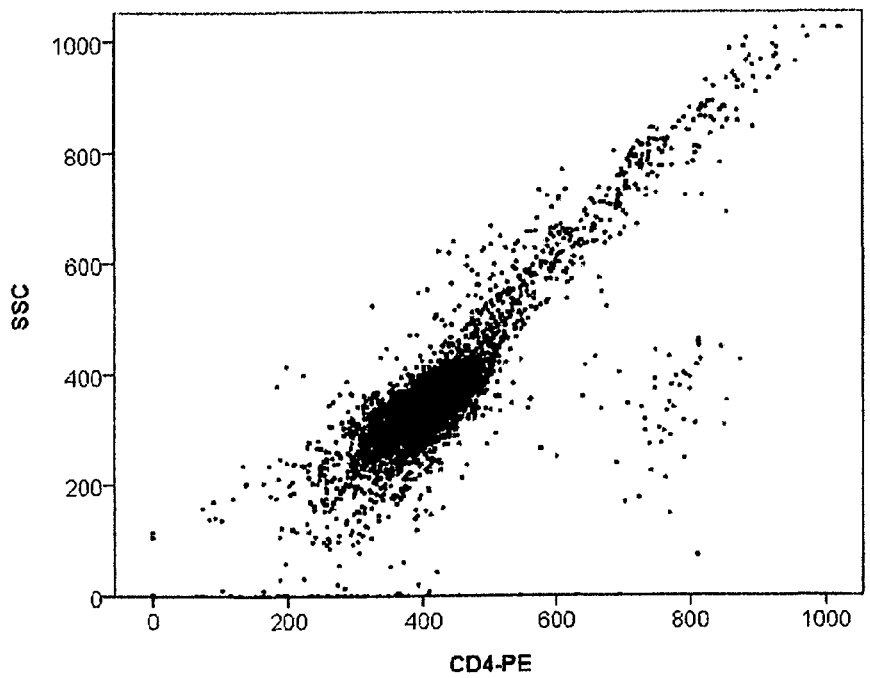

Non-stabilized leukocytes obtained from fresh blood (but not lyophilized) and stored for three days at 40° are not more active compared to the same leukocytes measured for activity directly after isolation (FIGS. 5A, 5B).

Figure 6A:
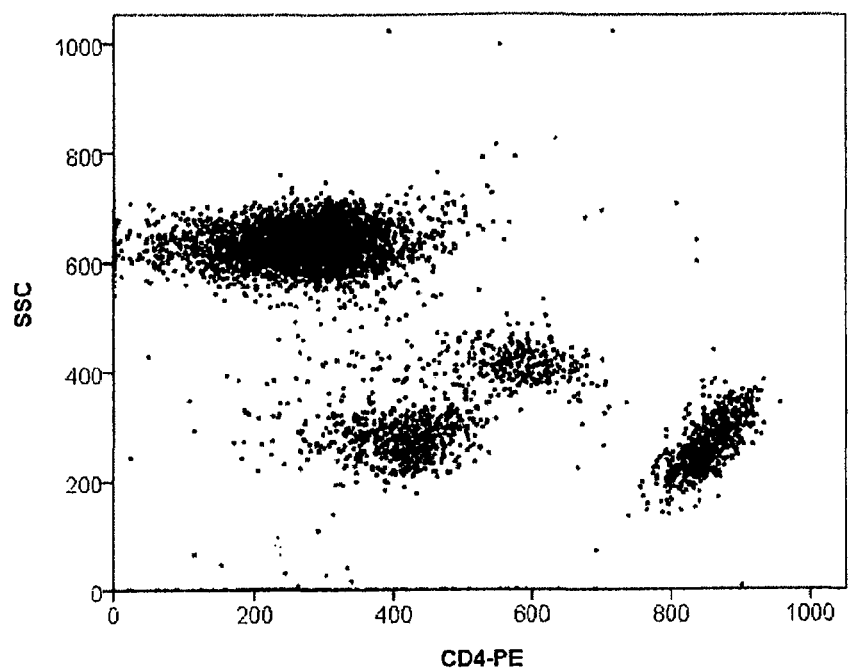
Figure 6B:
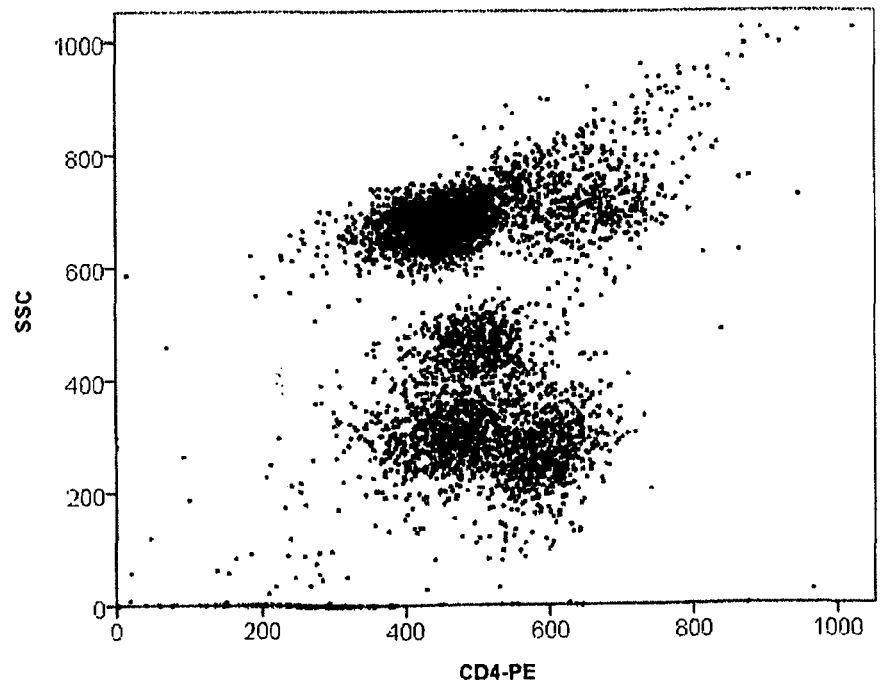

In contrast to that freshly isolated leukocytes preserved with a formaldehyde releasing agent, such as IU, having the same CD4+ activity as compared to non-preserved cells, are more stable after storage at 40° C. for 7 days than non-preserved cells, but cannot maintain their full activity under these conditions (FIGS. 6A, 6B).

Figure 7A:
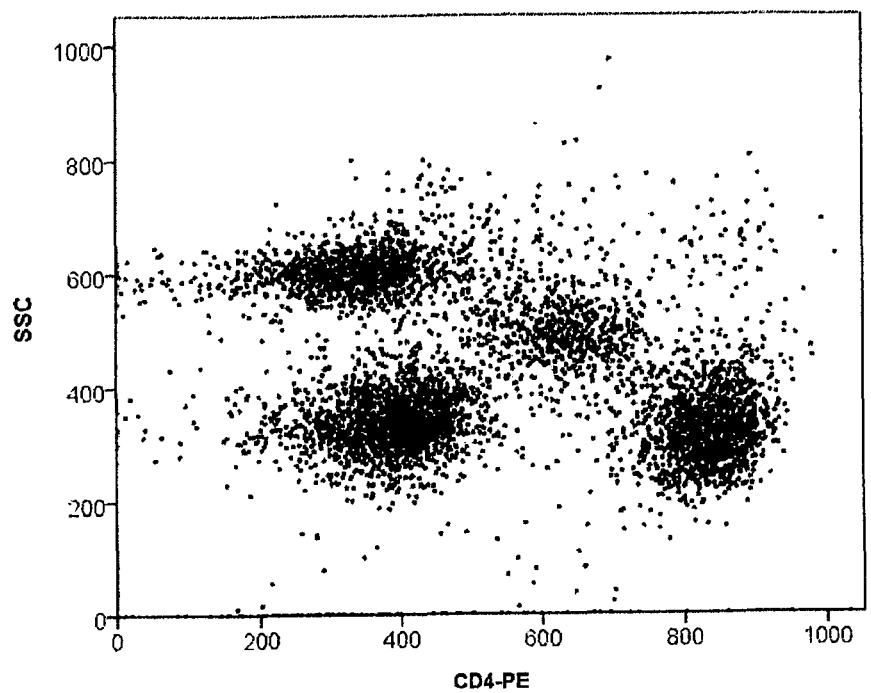
Figure 7B:
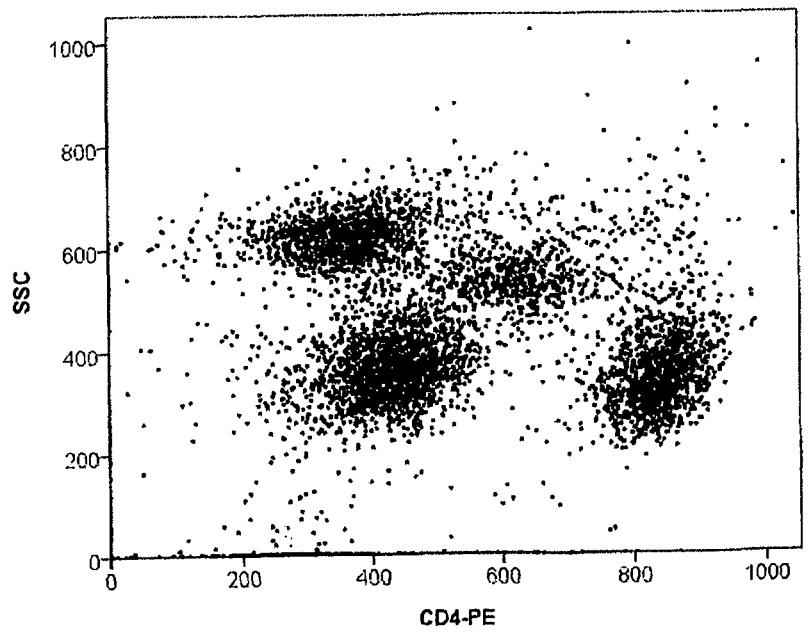
Figure 7C:
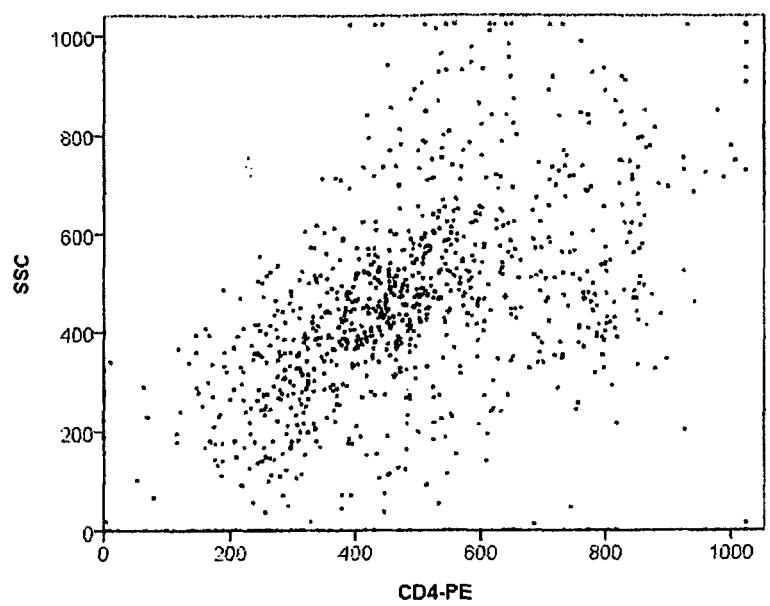

Surprisingly, leukocytes preserved by means of a formaldehyde releasing agent such as IU or DU, preferably IU, followed by lyophilization, and thus treated according to the method of the invention, are as stable as freshly isolated leukocytes even after 7 days storage at 40° C. (FIGS. 7A, 7B). Interestingly a sample of freshly isolated leukocytes that were directly lyophilized without any prior preservation by a formaldehyde releasing agent, has lost its complete CD4+ activity (FIG. 7C). This clearly shows that only leukocytes prepared by the regimen of the method as described reveal the superior properties with regard to stability over a long period under extreme temperature conditions.

In the following the best mode of the method of preparing of the stable leukocytes according to the invention is described. Alternatives or changes guaranteeing the general favorable teaching of this invention are included.

It is recommended and preferred according to this invention to prepare leukocytes from other blood components before preservation and lyophilzation. Nonetheless, in principle, it is possible also to use whole blood and to stabilize and lyophilize it according to the method described in more detail as follows.

In a preferred embodiment of the invention leukocytes are isolated from fresh blood samples before preservation with a formaldehyde releasing agent and subsequent lyophilization. Isolation and purification of intact and CD4+ active leukocytes can be achieved by any known suitable method. One effective and rapid alternative is to obtain leukocytes from blood by density gradient centrifugation. Different colloidal solutions are commercially available that can be adjusted to the necessary density which is required for the separation. For example, Percoll™ density gradient centrifugation between 700 and 1000×g, preferably 800×g or about 800×g for 15 to 30 minutes, preferably 20-25 minutes at room temperature (20-25° C.) can be carried out.

The leukocyte fraction from the density gradient centrifugation is directly taken or after eliminating the gradient material, for re-suspending with an aqueous solution of a formaldehyde releasing compound as specified above, preferably IU or DU, most preferably IU. A suitable solution comprises the formaldehyde releasing agent, such as IU or DU, in a concentration of 0.5-15% by weight of the overall composition, preferably 1-15%, more preferably 4-7%, more preferably 3-6%, and more preferably 3-4%. Generally, the concentration to be used depends also on the kind of the formaldehyde releasing agent and its preservation activity. The upper concentration limit is determined by the requirement that resulting stabilized leukocytes should not lose their CD4+ activity. The lower concentration limit is determined by a necessary sufficient stabilizing effect of the cells. Preferably the solution is buffered between pH7 and pH8 (pH7-pH8). Moreover, in further embodiments of the invention the stabilizing solution may also contain further agents generally known to stabilize biologic material, such as polyethylene glycol (e.g. PEG 20.000) in a concentration of 0.2-0.5, preferably 0.3% (w/w), EDTA (e.g. 0.005%-0.01%), and optionally human or bovine albumin.

The leukocytes are incubated with said stabilization solution preferably at a temperature of 0-10° C., preferably 4-6° C. The term of incubation may vary from 12 h-48 h. Preferably, the incubation time is 24-48 h, more preferably 24-36 h. The incubation term also depends on the kind of the selected formaldehyde releasing agent and its preservation activity.

After completion of the fixation of the cells the cells containing solution is directly used for lyophilization. The freezing temperature prior to lyophilization is preferably between −15° C. and −196° C. Preferably, the samples are lyophilized using liquid air or liquid nitrogen.

It has been found according to the invention that especially stable leukocytes can be obtained, if there is still a final moisture content after lyophilization. Thus, it is favorable to obtain a leukocyte preparation resulting from the lyophilization step with a water content between 0-4%, preferably between 1-3%, and most preferably of 3%, or approximately 3%.

For measurement of CD4+ activity, for example, by flow cytometry, the lyophilized stabilized cells are mixed or resuspended with distilled water or buffer solution.

SHORT DESCRIPTION OF THE FIGURES

FIG. 1

Flow cytometric appearance of native blood samples (A, C) and stabilized leukocytes (B, D). Two common methods for the determination of CD4+ T-cell count are shown (A-B, C-D). (A, B) Measurement of CD4 count and CD4 percentage using antibodies against CD4 (conjugated with phycoerythrin (PE)), CD45 (conjugated with fluorescein isothiocyanate (FITC)) and SSC (G1, lymphocytes; G2 CD4+ T-cells). Calculation of CD4 percentage is from the number of events in G2 divided by the number of events in G1 (C, D) Comparison of native blood and stabilized leukocytes at flow cytometric CD4 count using antibodies against CD4 (PE conjugated) and sideward scatter. CD4+ T-cells are separated in RN1 from the CD4+ weak monocytes.

FIG. 2

(2A) Long-term stability testing of lyophilized preserved leukocytes stored at 40° C. for 33 days. Re-suspended aliquots of freeze-dried leukocytes with two different concentrations of T-cells (sample A: 770±38 CD4+ T-cells; sample B: 620±22 CD4+ T-cells) were used for the flow cytometric analysis of CD4+ T-cells. Values are displayed as mean±SD.

(2B) Stability testing of lyophilized preserved leukocytes stored at 40° C. for 33 days. Re-suspended aliquots of freeze-dried leukocytes with two different concentrations of lymphocytes (sample A: 1596±87 CD4+ T-cells; sample B: 1452±53 CD4+ T-cells) were used for the flow cytometric analysis of CD4 percentage of lymphocytes. Values are displayed as mean±SD.

FIG. 3

(3A) Transportation time for internationally distributed test samples. Stabilized samples for the pilot survey were shipped from Germany to 21 countries within the African and Asian continents. The transportation time to the recipients varied from 1 week up to 4 weeks, with a mean shipping time of 14 days.

(3B) Test results of the international external quality control (pilot survey) for the CD4 count and CD4 percentage. Values obtained from the participants are subsequently displayed according to the method used. The code of the used method ((1) CD4 absolute; (2) CD4 percentage, see method/flow cytometry), the number of results (n), minimum and maximum value (Min, Max), 16$^{th}$ percentile, median and 84$^{th}$ percentile (16.P. 50P. 84.P.) are displayed. In addition, the position of the accepted range (I I) and the median, including the range between the 16.P and the 84.P (-I-), are graphically shown. The majority of participants (88 out of 95 (92.6%)) obtained acceptable results for CD4+ T-cells defined as SEM (standard error of mean) <26%.

FIG. 4

(4A) The diagram shows a Youden plot of the data received from the pilot survey. Displayed are the returned test values for CD4+ T-cells (target value of sample A: 1596±87 CD4+ T-cells; sample B: 1452±53 CD4+ T-cells) according to the age of the sample at the time of measurement (size of circle). No significant correlation between the age of the samples and variation from the target value was observed. (4B) Results from the pilot survey for CD4 percentage of lymphocytes. The diagram shows a Youden plot of the data received from the pilot survey. Displayed are the returned values for both test samples (target value of sample A and B: 47±3% CD4+ T-cells of lymphocytes) according to the age of the sample at the time of measurement (size of circle). No significant correlation between the age of the samples and variation from the target value was observed.

FIG. 5

(5A) Flow cytometric analysis of leukocytes from a non-stabilized blood directly after taking of the sample. Leukocytes were stained with PE-conjugated monoclonal antibody directed to CD4. The figure shows analyzed cells as a dot blot of SSC (sideward scatter) versus anti CD4-PE.

(5B) Flow cytometric analysis of leukocytes from a non-stabilized blood after a storage time of 3 days at 40° C. Leukocytes were stained with PE-conjugated monoclonal antibody directed to CD4. The figure shows analyzed cells as a dot blot of SSC (sideward scatter) versus anti CD4-PE.

FIG. 6

(6A) Flow cytometric analysis of leukocytes from a cellular sample that has been chemically stabilized with IDU. Measurement was carried out directly after preservation (day 0). Leukocytes were stained with PE-conjugated monoclonal antibody directed to CD4. The figure shows analyzed cells as a dot blot of SSC (sideward scatter) versus anti CD4-PE.

(6B) Flow cytometric analysis of leukocytes from a cellular sample that has been chemically stabilized with IDU. The sample has been stored at 40° C. for 7 days before measurement. Leukocytes were stained with PE-conjugated monoclonal antibody directed to CD4. The figure shows analyzed cells as a dot blot of SSC (sideward scatter) versus anti CD4-PE.

FIG. 7

(A) Flow cytometric analysis of leukocytes from a cellular sample that has been chemically stabilized with IDU and subsequently lyophilized. Measurement was carried out directly after lyophilization (day 0). Leukocytes were stained with PE-conjugated monoclonal antibody directed to CD4. The figure shows analyzed cells as a dot blot of SSC (sideward scatter) versus anti CD4-PE.

(B) Flow cytometric analysis of leukocytes from a cellular sample that has been chemically stabilized with IDU and subsequently lyophilized. The sample has been stored at 40° C. for 30 days before measurement. Leukocytes were stained with PE-conjugated monoclonal antibody directed to CD4. The figure shows analyzed cells as a dot blot of SSC (sideward scatter) versus anti CD4-PE.

(C) Flow cytometric analysis of non-stabilized leukocytes that have been directly lyophilized at day 0. The sample has been resuspended and measured directly after lyophilization. Leukocytes were stained with PE-conjugated monoclonal antibody directed to CD4. The figure shows analyzed cells as a dot blot of SSC (sideward scatter) versus anti CD4-PE.

EXAMPLES

Example 1

Preparation of Isolated Leukocytes from Blood Samples

Since erythrocytes and platelets are mainly undesirable cells for flow cytometric analysis that can have negative effects on the measurement especially after chemically preservation with commonly known fixatives (cell aggregates with leukocytes, adhesion effects on synthetic materials, etc.) these cells may be removed from blood samples used for stabilizing procedure. Leukocytes were separated from anti-coagulated blood by density gradient centrifugation. The most preferable solution is Percoll with an adjusted density of δ=1.095. Centrifugation is carried out at 800×g for 25 min at 25° C. Leukocytes revealed from the density gradient centrifugation are resuspended with a fixative solution.

Example 2

Stabilization with IU and Lyophilization of Isolated Leukocytes

Stabilization solution: The preservative agent was imidazolidinyl urea (IDU) in a buffered aqueous solution (PBS, pH 7.5). IDU was used at a concentration of 3% by weight of the overall composition. Additional components were 0.3% polyethylen glycol (PEG 20000) and 0.05% EDTA (percent by weight). In addition, albumin was added.

Leukocytes obtained as described in Example 1 were incubated in the above stabilizing solution of 36 h at 4° C. to obtain the desired shelf life. After completed incubation the solution was frozen in liquid nitrogen. The following lyophilization was carried out in such a way that a residual moisture content of approx. 2% was obtained.

Example 3

Stabilization with DU and Lyophilization of Isolated Leukocytes

The stabilization of isolated lycocytes was carried out as described in Example 2, however, instead of imidazolidinyl urea (IU) diazolidinyl urea (DU was used as stabilizing formaldehyde releasing agent.

Example 4

Flow Cytometry

Before usage the lyophilized cells were mixed with distilled water to generate a cell suspension with the initial volume.

Shelf life of the preserved leukocytes was analyzed using the basic CyFlow flow cytometer SL2 (Partec, Germany). Two commercially available protocols for single CD4 count (CD4 absolute kit, Partec) or the parallel determination of CD4 count and CD4 percentage (CD4% kit, Partec) were used. In accordance with the used protocol (CD4 absolute or CD4%) CD4+ T-cells were stained with anti-human CD4 (anti-CD4-PE, Partec) and analyzed together with their sideward scatter (SSC) (protocol: CD4 absolute) or additionally stained with anti-human CD45 (anti-CD-45-DY647, Partec) to monitor the integrity of the lyophilized leukocytes (protocol: CD4%) and their surface antigens relevant to clinical monitoring.

Example 5

Statistical Analysis

Statistical analysis was performed using the t-test and the Kolmogoroff-Smirnoff test where appropriate. Normality testing for Gaussian distribution of values was performed using the F-test. Student's t test and ANOVA were used to compare single or multiple data sets. p values of 0.05 or less were considered significant. Values are given as mean±standard deviation.

The invention claimed is:

1. An in-vitro method for stabilizing leukocytes, the method comprising the steps of: incubating leukocytes for at least 12 hours in a solution comprising a formaldehyde-releasing agent, followed by lyophilization of the incubation solution resulting in a long-term stable lyophilized preparation.

2. The method according to claim 1, wherein the incubating step is carried out for 24-48 hours.

3. The method according to claim 1, wherein the lyophilized leukocyte preparation has a residual moisture content between 0 and 3% (w/w).

4. The method according to claim 1, wherein the lyophilized leukocyte preparation has a residual moisture content of at least 1% (w/w).

5. The method according to claim 1, wherein the lyophilized leukocyte preparation has a residual moisture content of at least 2% (w/w).

6. The method according to claim 1, further comprising the step of dissolving or suspending the formaldehyde-releasing agent in an aqueous buffered solution prior to the incubating step.

7. The method according to claim 6, wherein the formaldehyde-releasing agent has a concentration of 2-10% (w/w).

8. The method according to claim 1, wherein the incubation solution comprises polyethylene glycol (PEG).

9. The method according to claim 1, wherein the formaldehyde-releasing agent is imidazolidinyl urea.

10. The method according to claim 1, further comprising the prior step of isolating a leukocyte fraction from a blood sample, or isolating a CD4+ receptor bearing cell population separated from the leukocyte fraction.

11. The method according to claim 10, wherein the leukocyte fraction or the CD4+ receptor bearing cell population is separated from other blood components of the blood sample by a density gradient centrifugation.

12. The method according to claim 11, wherein the density gradient centrifugation is carried out at 800-1000 g for at least 20 minutes in a density gradient medium at a density of $\delta=1.090$ to $1.100$.

13. The method according to claim 10, wherein the leukocyte fraction comprises at least one of lymphocytes and monocytes.

14. The method according to claim 13, wherein the leukocyte fraction further comprises granulocytes.

15. The method according to claim 11, wherein the leukocyte fraction is free of any granulocytes after density gradient centrifugation.

16. A long-term stable preparation of lyophilized leukocytes obtained by an in-vitro method comprising the steps of incubating leukocytes for at least 12 hours in a solution comprising a formaldehyde releasing agent, followed by lyophilization of the incubation solution resulting in a long-term stable lyophilized preparation.

17. The stable preparation according to claim 16, wherein the lyophilized product has a moisture content of 0-3% (w/w).

18. The stable preparation according to claim 16, wherein the stabilized lyophilized leukocytes are resuspendable in an aqueous solution after at least 4 weeks storage, and elicit full CD4+ T cell activity.

19. The stable preparation according to claim 16, wherein the stable preparation is used for diagnosis of a disease accompanied by a decrease or an increase of CD4+ T cells in the blood of a patient.

20. The stable preparation according to claim 19, wherein the disease is HIV/AIDS.

* * * * *